(12) United States Patent
Roth et al.

(10) Patent No.: US 8,767,069 B2
(45) Date of Patent: Jul. 1, 2014

(54) APPARATUS, SYSTEM, AND METHOD FOR INCREASING MEASUREMENT ACCURACY IN A PARTICLE IMAGING DEVICE USING LIGHT DISTRIBUTION

(75) Inventors: Wayne Dennis Roth, Leander, TX (US); Matthew S. Fisher, Austin, TX (US)

(73) Assignee: Luminex Corporation, Austin, TX (US)

( * ) Notice: Subject to any disclaimer, the term of this patent is extended or adjusted under 35 U.S.C. 154(b) by 971 days.

(21) Appl. No.: 12/827,837

(22) Filed: Jun. 30, 2010

(65) Prior Publication Data

US 2012/0002040 A1 Jan. 5, 2012

(51) Int. Cl.
*G06K 9/00* (2006.01)
*H04N 7/18* (2006.01)

(52) U.S. Cl.
USPC ... 348/135; 348/370; 348/E7.085; 356/237.3; 382/103; 250/458.1

(58) Field of Classification Search
None
See application file for complete search history.

(56) References Cited

U.S. PATENT DOCUMENTS

| | | | |
|---|---|---|---|
| 5,159,642 A | 10/1992 | Kosaka | 382/6 |
| 5,736,330 A | 4/1998 | Fulton | 435/6 |
| 5,981,180 A | 11/1999 | Chandler et al. | 435/6 |
| 6,057,107 A | 5/2000 | Fulton | 435/6 |
| 6,204,918 B1 * | 3/2001 | Isozaki et al. | 356/239.8 |
| 6,268,222 B1 | 7/2001 | Chandler et al. | 436/523 |
| 6,449,562 B1 | 9/2002 | Chandler et al. | 702/19 |
| 6,514,295 B1 | 2/2003 | Chandler et al. | 8/607 |
| 6,524,793 B1 | 2/2003 | Chandler et al. | 435/6 |
| 6,528,165 B2 | 3/2003 | Chandler | 428/402.2 |
| 6,649,414 B1 | 11/2003 | Chandler et al. | 436/63 |
| 6,939,720 B2 | 9/2005 | Chandler et al. | 436/518 |
| 7,079,708 B2 * | 7/2006 | Riley et al. | 382/294 |
| 7,274,809 B2 * | 9/2007 | MacAulay et al. | 382/128 |
| 7,286,719 B2 * | 10/2007 | Riley et al. | 382/294 |
| 7,643,143 B2 * | 1/2010 | Fujii et al. | 356/336 |
| 7,684,606 B2 * | 3/2010 | Aoki | 382/133 |
| 7,738,094 B2 * | 6/2010 | Goldberg | 356/246 |

(Continued)

FOREIGN PATENT DOCUMENTS

| | | |
|---|---|---|
| JP | 62-194448 | 8/1987 |
| JP | 2009-147122 | 6/1997 |

(Continued)

OTHER PUBLICATIONS

Akselli, B.; Kholmatov, A.; Nasibov, H., "The use of CCD pixel binning in PIV measurements," Optomechatronic Technologies, 2009. ISOT 2009. International Symposium on , pp. 223,228, Sep. 21-23, 2009.*

(Continued)

*Primary Examiner* — Christopher S Kelley
*Assistant Examiner* — Kaitlin A Retallick

(57) ABSTRACT

An apparatus, system, and method for increasing measurement accuracy in imaging cytometry. The system may include a light detector configured to measure light emitted by a particle in response to a first light source, and processor coupled to the light detector. The processor may be configured create a first image by taking a first measurement of light and create a second image by interpolating the first image, where the second image has higher resolution than the first image. The processor may be configured to determine a difference between pixels of the second image and an expected distribution and discard the first measurement of light if the difference is above a predetermined threshold.

22 Claims, 14 Drawing Sheets

(56) References Cited

U.S. PATENT DOCUMENTS

| | | | |
|---|---|---|---|
| 2003/0038812 A1* | 2/2003 | Bartell | 345/581 |
| 2006/0002634 A1* | 1/2006 | Riley et al. | 382/294 |
| 2007/0064990 A1 | 3/2007 | Roth | 382/128 |
| 2008/0087068 A1* | 4/2008 | Roth et al. | 73/1.34 |
| 2008/0181499 A1* | 7/2008 | Yang et al. | 382/174 |
| 2008/0212069 A1* | 9/2008 | Goldberg et al. | 356/36 |
| 2009/0066941 A1* | 3/2009 | Togashi et al. | 356/237.3 |
| 2010/0020315 A1* | 1/2010 | Togashi et al. | 356/237.3 |
| 2011/0228256 A1* | 9/2011 | Allier | 356/36 |
| 2012/0002194 A1 | 1/2012 | Roth et al. | 356/213 |

FOREIGN PATENT DOCUMENTS

| | | | | |
|---|---|---|---|---|
| JP | 2005-127790 | | 5/2005 | |
| JP | 2006-153709 | | 6/2006 | |
| JP | 2006-194788 | | 7/2006 | |
| JP | 2006-194788 A | * | 7/2006 | G01N 15/02 |
| JP | 2011-021948 | | 2/2011 | |

OTHER PUBLICATIONS

International Search Report and Written Opinion, issued in International Application No. PCT/US2011/042333, mailed on Feb. 29, 2012.

International Search Report and Written Opinion, issued in International Application No. PCT/US2011/042317, mailed on Feb. 29, 2012.

U.S. Appl. No. 12/827,800 entitled "Apparatus, System, and Method for Increasing Measurement Accuracy in a Particle Imaging Device," by Wayne Roth and Mathew Fisher, filed Jun. 30, 2010.

Patent Examination Report No. 1 in Australian Application No. 2011279976 issued Aug. 26, 2013, 3 pages.

\* cited by examiner

FIG. 11A

| 0 | 0 | 0 | 0 | 0 | 0 | 0 | 0 | 0 | 0 | 0 | 0 | 0 | 0 | 0 | 0 | 0 | 0 | 0 | 0 |
|---|---|---|---|---|---|---|---|---|---|---|---|---|---|---|---|---|---|---|---|
| 6 | 10 | 15 | 21 | 28 | 36 | 45 | 55 | 66 | 78 | 91 | 105 | 120 | 136 | 153 | 171 | 190 | 210 |
| 72 | 100 | 130 | 162 | 196 | 232 | 270 | 310 | 352 | 396 | 442 | 490 | 540 | 592 | 646 | 702 | 760 | 820 |
| 198 | 270 | 345 | 423 | 504 | 588 | 675 | 765 | 858 | 954 | 1053 | 1155 | 1260 | 1368 | 1479 | 1593 | 1710 | 1830 |
| 384 | 520 | 660 | 804 | 952 | 1104 | 1260 | 1420 | 1584 | 1752 | 1924 | 2100 | 2280 | 2464 | 2652 | 2844 | 3040 | 3240 |
| 630 | 850 | 1075 | 1305 | 1540 | 1780 | 2025 | 2275 | 2530 | 2790 | 3055 | 3325 | 3600 | 3880 | 4165 | 4455 | 4750 | 5050 |
| 636 | 860 | 1090 | 1326 | 1568 | 1816 | 2070 | 2330 | 2596 | 2868 | 3146 | 3430 | 3720 | 4016 | 4318 | 4626 | 4940 | 5260 |
| 702 | 950 | 1205 | 1467 | 1736 | 2012 | 2295 | 2585 | 2882 | 3186 | 3497 | 3815 | 4140 | 4472 | 4811 | 5157 | 5510 | 5870 |
| 828 | 1120 | 1420 | 1728 | 2044 | 2368 | 2700 | 3040 | 3388 | 3744 | 4108 | 4480 | 4860 | 5248 | 5644 | 6048 | 6460 | 6880 |
| 1014 | 1370 | 1735 | 2109 | 2492 | 2884 | 3285 | 3695 | 4114 | 4542 | 4979 | 5425 | 5880 | 6344 | 6817 | 7299 | 7790 | 8290 |
| 1260 | 1700 | 2150 | 2610 | 3080 | 3560 | 4050 | 4550 | 5060 | 5580 | 6110 | 6650 | 7200 | 7760 | 8330 | 8910 | 9500 | 10100 |
| 1266 | 1710 | 2165 | 2631 | 3108 | 3596 | 4095 | 4605 | 5126 | 5658 | 6201 | 6755 | 7320 | 7896 | 8483 | 9081 | 9690 | 10310 |
| 1332 | 1800 | 2280 | 2772 | 3276 | 3792 | 4320 | 4860 | 5412 | 5976 | 6552 | 7140 | 7740 | 8352 | 8976 | 9612 | 10260 | 10920 |
| 1458 | 1970 | 2495 | 3033 | 3584 | 4148 | 4725 | 5315 | 5918 | 6534 | 7163 | 7805 | 8460 | 9128 | 9809 | 10503 | 11210 | 11930 |
| 1644 | 2220 | 2810 | 3414 | 4032 | 4664 | 5310 | 5970 | 6644 | 7332 | 8034 | 8750 | 9480 | 10224 | 10982 | 11754 | 12540 | 13340 |
| 1890 | 2550 | 3225 | 3915 | 4620 | 5340 | 6075 | 6825 | 7590 | 8370 | 9165 | 9975 | 10800 | 11640 | 12495 | 13365 | 14250 | 15150 |
| 1896 | 2560 | 3240 | 3936 | 4648 | 5376 | 6120 | 6880 | 7656 | 8448 | 9256 | 10080 | 10920 | 11776 | 12648 | 13536 | 14440 | 15360 |
| 1962 | 2650 | 3355 | 4077 | 4816 | 5572 | 6345 | 7135 | 7942 | 8766 | 9607 | 10465 | 11340 | 12232 | 13141 | 14067 | 15010 | 15970 |
| 2088 | 2820 | 3570 | 4338 | 5124 | 5928 | 6750 | 7590 | 8448 | 9324 | 10218 | 11130 | 12060 | 13008 | 13974 | 14958 | 15960 | 16980 |
| 2274 | 3070 | 3885 | 4719 | 5572 | 6444 | 7335 | 8245 | 9174 | 10122 | 11089 | 12075 | 13080 | 14104 | 15147 | 16209 | 17290 | 18390 |
| 2520 | 3400 | 4300 | 5220 | 6160 | 7120 | 8100 | 9100 | 10120 | 11160 | 12220 | 13300 | 14400 | 15520 | 16660 | 17820 | 19000 | 20200 |

FIG. 11B

| 0 | 0 | 0 | 0 | 0 | 0 | 0 | 0 | 0 | 0 | 0 | 0 | 0 | 0 | 0 | 0 | 0 | 0 |
|---|---|---|---|---|---|---|---|---|---|---|---|---|---|---|---|---|---|
| 6 | 10 | 15 | 21 | 28 | 36 | 45 | 55 | 66 | 78 | 91 | 105 | 120 | 136 | 153 | 171 | 190 | 210 |
| 72 | 100 | 130 | 162 | 196 | 232 | 270 | 310 | 352 | 396 | 442 | 490 | 540 | 592 | 646 | 702 | 760 | 820 |
| 198 | 270 | 345 | 423 | 504 | 588 | 675 | 765 | 858 | 954 | 1053 | 1155 | 1260 | 1368 | 1479 | 1593 | 1710 | 1830 |
| 384 | 520 | 660 | 804 | 952 | 1104 | 1260 | 1420 | 1584 | 1752 | 1924 | 2100 | 2280 | 2464 | 2652 | 2844 | 3040 | 3240 |
| 630 | 850 | 1075 | 1305 | 1540 | 1780 | 2025 | 2275 | 2530 | 2790 | 3055 | 3325 | 3600 | 3880 | 4165 | 4455 | 4750 | 5050 |
| 636 | 860 | 1090 | 1326 | 1568 | 1816 | 2070 | 2330 | 2596 | 2868 | 3146 | 3430 | 3720 | 4016 | 4318 | 4626 | 4940 | 5260 |
| 702 | 950 | 1205 | 1467 | 1736 | 2012 | 2295 | 2585 | 2882 | 3186 | 3497 | 3815 | 4140 | 4472 | 4811 | 5157 | 5510 | 5870 |
| 828 | 1120 | 1420 | 1728 | 2044 | 2368 | 2700 | 3040 | 3388 | 3744 | 4108 | 4480 | 4860 | 5248 | 5644 | 6048 | 6460 | 6880 |
| 1014 | 1370 | 1735 | 2109 | 2492 | 2884 | 3285 | 3695 | 4114 | 4542 | 4979 | 5425 | 5880 | 6344 | 6817 | 7299 | 7790 | 8290 |
| 1260 | 1700 | 2150 | 2610 | 3080 | 3560 | 4050 | 4550 | 5060 | 5580 | 6110 | 6650 | 7200 | 7760 | 8330 | 8910 | 9500 | 10100 |
| 1266 | 1710 | 2165 | 2631 | 3108 | 3596 | 4095 | 4605 | 5126 | 5658 | 6201 | 6755 | 7320 | 7896 | 8483 | 9081 | 9690 | 10310 |
| 1332 | 1800 | 2280 | 2772 | 3276 | 3792 | 4320 | 4860 | 5412 | 5976 | 6552 | 7140 | 7740 | 8352 | 8976 | 9612 | 10260 | 10920 |
| 1458 | 1970 | 2495 | 3033 | 3584 | 4148 | 4725 | 5315 | 5918 | 6534 | 7163 | 7805 | 8460 | 9128 | 9809 | 10503 | 11210 | 11930 |
| 1644 | 2220 | 2810 | 3414 | 4032 | 4664 | 5310 | 5970 | 6644 | 7332 | 8034 | 8750 | 9480 | 10224 | 10982 | 11754 | 12540 | 13340 |
| 1890 | 2550 | 3225 | 3915 | 4620 | 5340 | 6075 | 6825 | 7590 | 8370 | 9165 | 9975 | 10800 | 11640 | 12495 | 13365 | 14250 | 15150 |
| 1896 | 2560 | 3240 | 3936 | 4648 | 5376 | 6120 | 6880 | 7656 | 8448 | 9256 | 10080 | 10920 | 11776 | 12648 | 13536 | 14440 | 15360 |
| 1962 | 2650 | 3355 | 4077 | 4816 | 5572 | 6345 | 7135 | 7942 | 8766 | 9607 | 10465 | 11340 | 12232 | 13141 | 14067 | 15010 | 15970 |
| 2088 | 2820 | 3570 | 4338 | 5124 | 5928 | 6750 | 7590 | 8448 | 9324 | 10218 | 11130 | 12060 | 13008 | 13974 | 14958 | 15960 | 16980 |
| 2274 | 3070 | 3885 | 4719 | 5572 | 6444 | 7335 | 8245 | 9174 | 10122 | 11089 | 12075 | 13080 | 14104 | 15147 | 16209 | 17290 | 18390 |
| 2520 | 3400 | 4300 | 5220 | 6160 | 7120 | 8100 | 9100 | 10120 | 11160 | 12220 | 13300 | 14400 | 15520 | 16660 | 17820 | 19000 | 20200 |

APPARATUS, SYSTEM, AND METHOD FOR INCREASING MEASUREMENT ACCURACY IN A PARTICLE IMAGING DEVICE USING LIGHT DISTRIBUTION

BACKGROUND OF THE INVENTION

1. Field of the Invention

This invention relates to methods and systems for image data processing. Some embodiments relate to methods and systems for performing one or more steps for processing images of particles.

2. Description of the Related Art

Imaging using detectors such as charged coupled device (CCD) detectors is used in biotechnology applications. In some applications, the CCDs are configured to measure fluorescent light emitted by particles in response to a light source. Particles may have different intensities of fluorescence depending on how much of a particular fluorescent substance is present. The amount of fluorescent substance may be indicative of several conditions. For example, the amount of fluorescence may indicate the presence or absence of a substance, or the absorption of a particular substance by a particle.

SUMMARY OF THE INVENTION

A method for increasing the measurement accuracy in a particle imaging device is presented. In one embodiment, the method may include measuring light emitted by a first particle and measuring light emitted by a second particle, where the measured light from the second particle at least partially overlaps the measured light from the first particle in an overlap region. In some embodiments, the method may include determining a contribution of light from the first particle in the overlap region and determining a contribution of light from the second particle in the overlap region. Additionally, the method may include subtracting the contribution of light from the second particle from the contribution of light from the first particle, and determining the intensity of light emitted by the first particle.

In some embodiments, measuring light emitted by the first particle and the second particle may be performed using a two dimensional CCD detector. In some embodiments, the light detector may be a CMOS detector or a quantum dot detector. Also, in some embodiments, determining the contribution of light from the second particle in the overlap region may include calculating a Gaussian distribution of light from the second particle. In some embodiments, at least a portion of the measured light from the second particle is reflected off of the first particle. Determining the contribution of light from the second particle in the overlap region may include calculating the light from the second particle that is reflected off the first particle. In addition, determining the contribution of light from the second particle may include measuring a distance between the first particle and the second particle. Determining the amount of measured light from the second particle may include measuring an intensity of the second particle. In some embodiments, the method may include discarding the measurement of the first particle.

A method for increasing the measurement accuracy in a particle measurement device is also presented. In some embodiments, the method includes measuring light emitted by a first particle and measuring light emitted by a second particle, where at least a portion of light emitted by the second particle is reflected off of the first particle. The method may also include determining a contribution of light from the second particle that reflected off of the first particle, and/or discarding the measurement of the first particle. In some embodiments, the measurement of the first particle may be discarded if the contribution of light from the second particle that reflected off of the first particle is above a predetermined value. In some embodiments, determining the contribution of light from the second particle that has reflected off of the first particle includes measuring a distance between the first particle and the second particle. Additionally, the method may include determining the relative intensity between the two particles.

A tangible computer-readable medium comprising computer readable code, that when executed by a computer, causes the computer to perform operations is also presented. In some embodiments, the operations may include measuring light emitted by a first particle and measuring light emitted by a second particle, where the measured light from the second particle at least partially overlaps the measured light from the first particle in an overlap region. Also, the operations may include determining a contribution of light from the first particle in the overlap region and/or determining a contribution of light from the second particle in the overlap region. In some embodiments, the operations may include subtracting the contribution of light from the second particle from the contribution of light from the first particle and determining the intensity of light emitted by the first particle.

In some embodiments, the operations of measuring light emitted by the first particle and the second particle may be performed using a CCD detector, CMOS detector, and/or a quantum dot detector. Also, the operations may include determining the contribution of light from the second particle in the overlap region, which may include calculating a Gaussian distribution of light from the second particle.

In some embodiments, at least a portion of the measured light from the second particle is reflected off the first particle. In some embodiments, the operation of determining the contribution of light from the second particle in the overlap region may include calculating the light from the second particle that is reflected off the first particle. The operations of determining the contribution of light from the second particle may include measuring a distance between the first particle and the second particle. In some embodiments, the operations of determining the amount of measured light from the second particle further may include measuring an intensity of the second particle. In some embodiments, the operations may include discarding the measurement of the first particle.

An optical analysis system is also presented. In some embodiments, the system may include a light detector configured to measure light emitted by a first particle and light emitted by a second particle, where the measured light from the second particle at least partially overlaps the measured light from the first particle in an overlap region. Additionally, the system may include a processor coupled to the light detector, where the processor is configured to determine a contribution of light from the first particle in the overlap region and determine a contribution of light from the second particle in the overlap region. The processor may also be configured to subtract the contribution of light from the second particle from the contribution of light from the first particle and determine the intensity of light emitted by the first particle.

In some embodiments, the light detector may be a CCD detector, CMOS detector, and/or a quantum dot detector. Also, the processor may be configured to calculate a Gaussian distribution of light from the second particle to determine the contribution of light from the second particle in the overlap region. Additionally, the processor may be configured to calculate the light from the second particle that is reflected off the first particle and may determine the contribution of light from the second particle in the overlap region. In some embodiments, the processor may be further configured to measure a distance between the first particle and the second particle to determine the contribution of light from the second particle. Also, the processor may be configured to measure an intensity of the second particle to determine the amount of measured light from the second particle. In some embodiments, the processor may be configured to discard the measurement of the first particle.

A method for increasing the measurement accuracy in a particle imaging device is also presented. In some embodiments, the method may include illuminating a particle using a first light source and creating a first image by taking a first measurement of light emitted from the particle in response to the first light source using a light detector. The method may also include creating a second image by interpolating the first image, where the second image has higher resolution than the first image. Additionally, the method may include determining the center of the particle in the second image.

In some embodiments the method may include determining the intensity of the particle by integrating the second image. Additionally, the method may include creating an analytical representation of the first measurement of light and determining the intensity of the particle by integrating the analytical representation. In some embodiments, the method may include determining a difference between pixels of the second image and an expected distribution, and discarding the first measurement of light if the difference is above a predetermined threshold.

In some embodiments, the expected distribution may be a Gaussian distribution. The method may also include illuminating the particle with a second light source, and creating a third image by taking a second measurement of light emitted by the particle in response to the second light source using the light detector. Additionally, the method may include determining the center of the particle in the third image and determining a difference in location between the center of the particle in the second image and the center of the particle in the third image. In some embodiments, the method may include calculating an offset between the second image and the third image in response to the difference.

In some embodiments, the method may include aligning the first image and the third image. Also, the method may include using a plurality of particles to calculate the offset between the second image and the third image.

A tangible computer readable medium comprising computer readable code, that when executed by a computer, causes the computer to perform operations is also presented. In some embodiments, the operations may include illuminating a particle using a first light source and creating a first image by taking a first measurement of light emitted from the particle in response to the first light source using a light detector. Additionally, the operations may include creating a second image by interpolating the first image, where the second image has higher resolution than the first image, and determining the center of the particle in the second image.

In some embodiments, the operations may include determining the intensity of the particle by integrating the second image. The operations may also include creating an analytical representation of the first measurement of light and determining the intensity of the particle by integrating the analytical representation. Also, the operations may include determining a difference between pixels of the second image and an expected distribution, and discarding the first measurement of light if the difference is above a predetermined threshold.

In some embodiments, the expected distribution is a Gaussian distribution. Also, the operations may include illuminating the particle with a second light source, creating a third image by taking a second measurement of light emitted by the particle in response to the second light source using the light detector, and/or determining the center of the particle in the third image. In some embodiments the operations may include determining a difference in location between the center of the particle in the second image and the center of the particle in the third image and/or calculating an offset between the second image and the third image in response to the difference. In some embodiments, the operations may include aligning the first image and the third image. Also, the operations may include using a plurality of particles to calculate the offset between the second image and the third image.

An optical analysis system is also presented. In some embodiments, the system may include a light detector configured to measure light emitted by a particle in response to a first light source, and processor coupled to the light detector. The processor may be configured create a first image by taking a first measurement of light and create a second image by interpolating the first image, where the second image has higher resolution than the first image. The processor may also be configured to determine the center of the particle in the second image.

In some embodiments, the processor may be configured to determine the intensity of the particle by integrating the second image. Additionally, the processor may be configured to create an analytical representation of the first measurement of light and determine the intensity of the particle by integrating the analytical representation. In some embodiments, the processor is further configured to determine a difference between pixels of the second image and an expected distribution and discard the first measurement of light if the difference is above a predetermined threshold. In some embodiments, the expected distribution is a Gaussian distribution.

In some embodiments, the processor may be further configured to illuminate the particle with a second light source and/or create a third image by taking a second measurement of light emitted by the particle in response to the second light source using the light detector. Additionally, the processor may be configured to determine the center of the particle in the third image, determine a difference in location between the center of the particle in the second image and the center of the particle in the third image, and/or calculate an offset between the second image and the third image in response to the difference.

In some embodiments, the processor may be further configured to align the first image and the third image. Additionally, the processor may be further configured to use a plurality of particles to calculate the offset between the second image and the third image. In some embodiments, the processor may be configured to calculate the offset between the first image and the third image.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 11A is a matrix representative of an output of a CCD detector.

FIGS. 11B-11D are matrices showing steps used in data manipulation.

DETAILED DESCRIPTION

Figure 1:
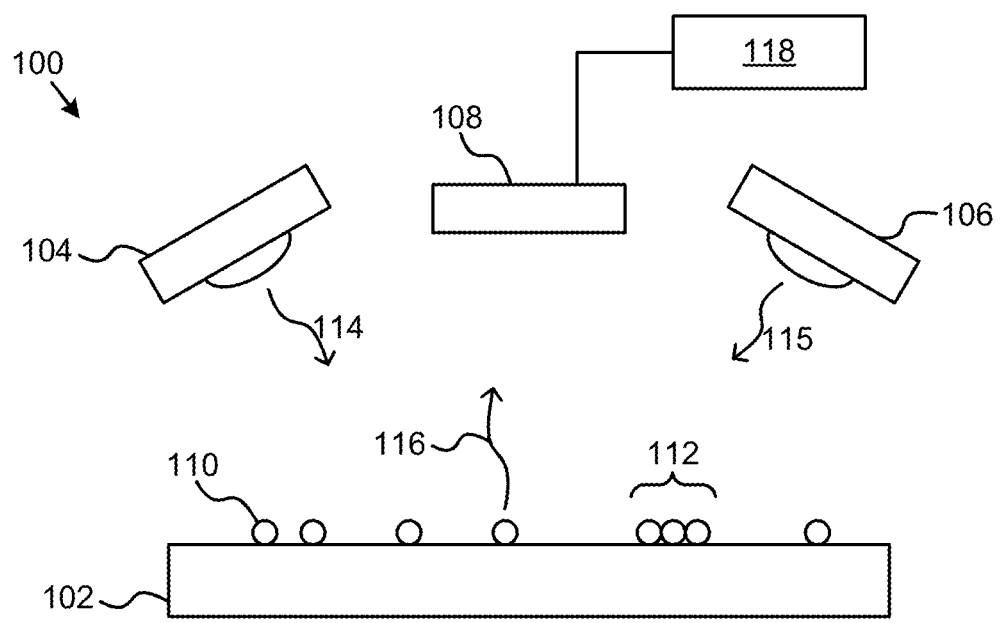
FIG. 1 is a schematic block diagram illustrating one embodiment of a system for imaging cytometry.

Various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Although embodiments are described herein with respect to particles, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated and described in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The systems and methods described herein may be used with any of the particles described in these patents. In addition, particles for use in method and system embodiments described herein may be obtained from manufacturers such as Luminex Corporation of Austin, Tex. The terms "particles", "beads", and "microspheres" are used interchangeably herein.

In addition, the types of particles that are compatible with the systems and methods described herein include particles with fluorescent materials attached to, or associated with, the surface of the particles. These types of particles, in which fluorescent dyes or fluorescent particles are coupled directly to the surface of the particles in order to provide the classification fluorescence (i.e., fluorescence emission measured and used for determining an identity of a particle or the subset to which a particle belongs), are illustrated and described in U.S. Pat. No. 6,268,222 to Chandler et al. and U.S. Pat. No. 6,649,414 to Chandler et al., which are incorporated by reference as if fully set forth herein. The types of particles that can be used in the methods and systems described herein also include particles having one or more fluorochromes or fluorescent dyes incorporated into the core of the particles.

Particles that can be used in the methods and systems described herein further include particles that in of themselves will exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles. As described below, image data processing may include classification of the particles, particularly for a multi-analyte fluid, as well as a determination of the amount of analyte bound to the particles. Since a reporter signal, which represents the amount of analyte bound to the particle, is typically unknown during operations, specially dyed particles, which not only emit fluorescence in the classification wavelength(s) or wavelength band(s) but also in the reporter wavelength or wavelength band, may be used for the processes described herein.

The methods described herein generally include analyzing one or more images of particles and processing data measured from the images to determine one or more characteristics of the particles, such as but not limited to numerical values representing the magnitude of fluorescence emission of the particles at multiple detection wavelengths. Subsequent processing of the one or more characteristics of the particles, such as using one or more of the numerical values to determine a token ID representing the multiplex subset to which the particles belong and/or a reporter value representing a presence and/or a quantity of analyte bound to the surface of the particles, can be performed according to the methods described in U.S. Pat. No. 5,736,330 to Fulton, U.S. Pat. No. 5,981,180 to Chandler et al., U.S. Pat. No. 6,449,562 to Chandler et al., U.S. Pat. No. 6,524,793 to Chandler et al., U.S. Pat. No. 6,592,822 to Chandler, U.S. Pat. No. 6,939,720 to Chandler et al., U.S. Patent Publication 2007/0064990, which are incorporated by reference as if fully set forth herein. In one example, techniques described in U.S. Pat. No. 5,981,180 to Chandler et al. may be used with the fluorescent measurements described herein in a multiplexing scheme in which the particles are classified into subsets for analysis of multiple analytes in a single sample. In one embodiment, the methods described herein can be used in a MagPix molecular diagnostics instrument. MagPix is a fluorescence microscope with automated image processing software that measures fluorescent intensity of thousands of randomly distributed magnetic beads.

Turning now to the figures, FIG. 1 illustrates a system 100 for imaging cytometry. It should be noted that FIG. 1 is now drawn to scale and some elements of the system are not shown so as to not obscure the system in detail.

The system has an imaging chamber 102 that may have one or more particles 110. As seen in FIG. 1, the particles 110 may not be evenly distributed along the imaging chamber 102, and may result in some particles being close together, such as the group of particles 112. In some embodiments the particles will be randomly distributed. Therefore, the more particles present on the imaging chamber 102, the higher the probability that two particles will be close together. FIG. 1 also shows a first light source 104 and a second light source 106, where the light sources are configured to illuminate particles 110 on the imaging chamber 102. In some embodiments, these light sources may be light emitting diodes (LEDs). The first light source 104 may have a different color (or wavelength of emitted light) than the second light source 106. Light ray 114 represents light emitted by the first light source 104. The light ray 114 may then illuminate the particles 110, which may fluoresce. The fluorescent light created by the particles 110 may then emit toward the light detector 108. Light ray 116 in FIG. 1 represents the fluorescent light emitted by a particle 110.

The light detector 108 is configured to detect fluorescent light emitted by the particles 110. The light detector may be a CCD detector, CMOS detector, quantum dot detector, or other detector. In some embodiments, it is beneficial for the light detector 108 to have low noise, and high resolution. The CCD detector may be a two dimensional array of pixels that creates a two dimensional image. For example, a CCD detector that may be used in this application is the Kodak KAI-4021.

In some cases, two or more particles may be close together. In such cases, the measured light in the light detector 108 may be close together and may even overlap. Therefore, in such a case where two or more particles are close together, there may be a pixel that measures light from two different particles. In an effort to increase the measurement accuracy of the system, the overlap of the light from the two different particles may be subtracted to determine the light contribution from each particle. Alternatively, measurements of overlapping particles can be discarded after the overlap is detected.

The light detector 108 is coupled to a processor 118. The processor is configured to take raw data from the CCD detector and process that data to obtain useful data about the particles 110. In some embodiments the processor may be a dedicated processor with necessary memory, data storage device, and input/output device, or it may be a personal computer that is programmed to perform the functions described herein. The data storage device used by the processor is a tangible storage medium such as a hard drive, an optical drive, or a flash memory device. The input/output device may be a monitor that outputs information to a user, or it may be a communication device, such as an Ethernet controller, that allows information gathered about the particles 110 to be sent to a remote location. Additionally, a printer may be used to output data into a tangible form.

Figure 2A:
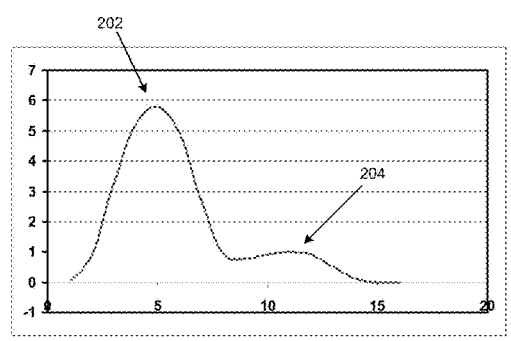
FIGS. 2A-2B are a graphs showing the light distribution of two nearby particles.

Turning to FIG. 2A, light emitted from two particles are shown in one dimension. There is a peak of light from particle 202 and a peak of light from particle 204. In this example, the intensity of light from particle 202 is significantly higher than the intensity of light from the particle 204. However, the two particles overlap slightly and the light from the particle 202 contributes to the light measured from the particle 204. In some embodiments, the light attributed to the particle 204 may be subtracted from the light attributed to the particle 202. Therefore, the measurement for particle 202 may be closer to what the measurement of the particle would have been if the particle 204 were not present. One advantage of this method is that more particles may be measured accurately, thereby increasing the overall accuracy of the system.

Figure 2B:
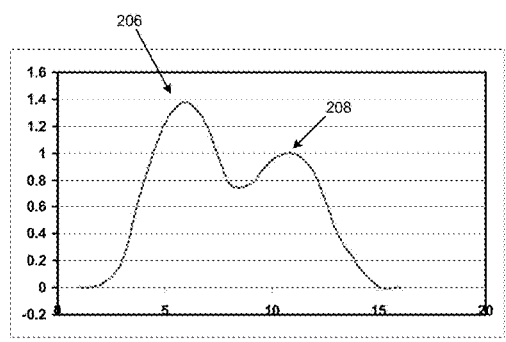

Turning to FIG. 2B, this graph also shows light emitted from two particles that are close together. However, the intensity of particle 206 is relatively similar to the intensity of light from the particle 208. As seen in this figure, there is significantly more overlap between these two particles, and determining the contribution of light from particle 208 to particle 206 may be more difficult. In this situation, the two measurements for the particles may be discarded. Alternatively, the distributions of the particles may be approximated using a standard Gaussian distribution based on the measured peaks and the slopes of the particles are least affected by the other particles. For example, the peak of particle 206 and/or the left slope of particle 206 may be used to approximate the expected distribution of particle 206. That expected distribution can then be used to determine the intensity of light emitted by particle 206, rather than the measure light on both sides of the peak of particle 206 (which includes light from particle 208). The same (although a mirror image) process may be used with particle 208 to determine the intensity of particle 208 without the contribution of particle 206. By subtracting the contribution of the neighboring particle, more particles may be measured, thereby increasing the accuracy of the system.

Figure 3:
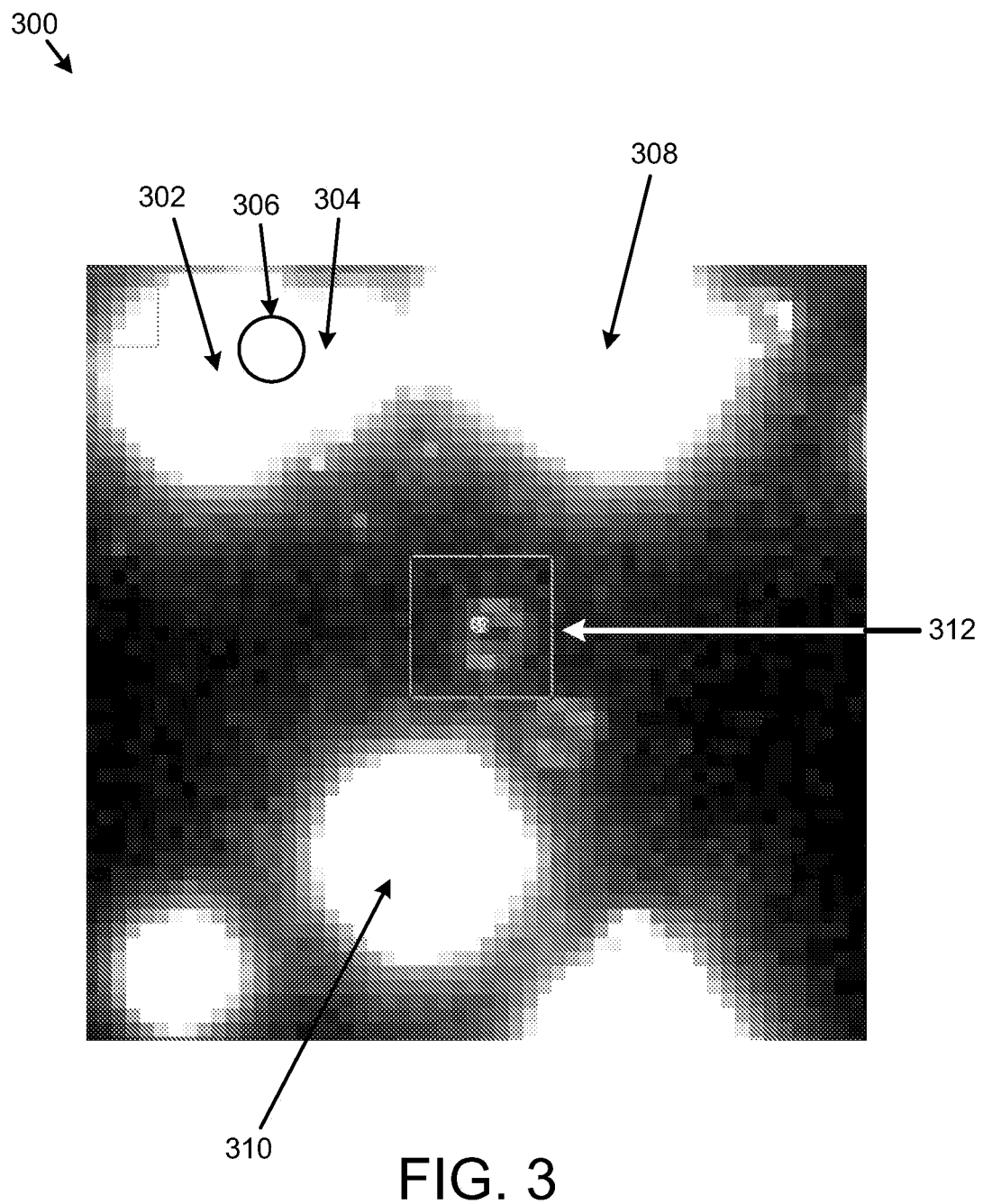
FIG. 3 is a measurement of particles taken with a CCD detector.

Turning to FIG. 3, a measurement 300 of several particles using a CCD detector is shown. For example, there is a particle 302 and a particle 304 that overlap in the overlap region 306. Using methods as described herein, particles 302 and 304 may be able to be accurately measured even though the particles are close together.

FIG. 3 also shows another situation where one particle may contribute light to the pixels measuring light from another particle. Particles 308 and 310 are relatively bright particles, as seen from the white spots near their centers. Between particles 308 and 310 is another particle 312, although particle 312 is much dimmer. One aspect of particle 312 is that the center is dimmer than the perimeter. Typically, if a particle is substantially round, the measured light will be brightest in the center. In particle 312, however, the edges are nearest to particles 308 and 310 are brighter than the center of particle 312. This light measured on the edges of particle 312 is caused by reflection or refraction from particles 308 and 310. In order to get an accurate measurement of the light actually produced by particle 312, the contributions from particles 308 and 310 must be subtracted. One way of subtracting the contribution of light from reflection is to calculate the amount of light that would be expected to reflect off the surface of a nearby particle. In some embodiments, the method of calculating the expected light includes measuring the distance of the nearby particle. In FIG. 3, the closer that particle 308 is to particle 312, the more light is expected to be reflected off the surface of particle 312. Also, the brighter that particle 308 is, the more light is expected to reflect off of the surface of particle 312. Other parameters, such as the medium of suspension or the material and size of the particles may affect how much light is reflected, and therefore may be used to calculate the amount of light that is expected to reflect off the surface of a particle.

In addition to light that is reflected off the surface of a particle, light may also be refracted through a particle, or through the surface of a particle. Because the indexes of refraction may be different between the particle and the medium of suspension, light may enter the particle at one angle and exit at another. Therefore, light from particle 308 may travel substantially towards particle 312 and refract through particle 312 and end up in the light detector 108.

In some embodiments, a particle may be discarded because of its proximity to a particle with much higher intensity. Because of proximity and relatively large difference in intensity between particle 308 and 312, particle 312 may be discarded from the measurement. By discarding a measurement known to have error, the accuracy of the overall system may be improved. In some embodiments, a table may be used to determine when a measurement should be discarded. The farther away a neighboring particle is, the more intense it can be before the measurement of a particle is discarded. Because the emission intensity of an omnidirectional radiator falls off at a rate of the square of the distance, the allowable intensity of a neighboring particle may increase with the square of the distance. Table 1 shows one example of the relationship between distance and intensity that can be used to determine when a particle should be discarded. The scale of the intensity is only shown in relative terms and does represent an actual unit of light intensity. The relationship of the values in Table 1 follow the expected dissipation of light and distance of $1/r^2$. For example, the threshold for discarding a particle that is twenty pixels away is four times as much as the threshold for discarding a particle that is ten pixels away. This table is given by way of example and not limitation.

TABLE 1

| Distance (pixels) | Difference (intensity) |
|---|---|
| 1 | 1 |
| 2 | 4 |
| 3 | 9 |
| 4 | 16 |
| 5 | 25 |
| 6 | 36 |
| 7 | 49 |
| 8 | 64 |
| 9 | 81 |

TABLE 1-continued

| Distance (pixels) | Difference (intensity) |
|---|---|
| 10 | 100 |
| 11 | 121 |
| 12 | 144 |
| 13 | 169 |
| 14 | 196 |
| 15 | 225 |
| 16 | 256 |
| 17 | 289 |
| 18 | 324 |
| 19 | 361 |
| 20 | 400 |

In some embodiments, other relationships of intensity and distance may be used to determine whether a particle measurement should be discarded. For example, Table 2 shows relative intensities that may be used to discard measurements. In this example, the intensities (also shown in relative terms), may be derived empirically and may represent raw values of individual pixel differences. For example, if an individual pixel value on a particle that is six pixels away is more than 7000 "units" larger than the peak pixel on a particle of interest, the particle of interest may be discarded because the intensity of the neighboring particle is likely to negatively affect the measurement. Also in this example, any neighboring pixels within a distance of 4 pixels from the peak pixel of the particle of interest are ignored, as those nearby pixels are presumed to lie within the dimensions of the particle of interest itself. Also, for example, if the peak to pixel distance is 20 pixels apart, neither should be discarded regardless of the difference between their intensities.

TABLE 2

| Distance (pixels) | Difference (intensity) |
|---|---|
| 1 | Infinity |
| 2 | Infinity |
| 3 | Infinity |
| 4 | Infinity |
| 5 | 3000 |
| 6 | 7000 |
| 7 | 15000 |
| 8 | 30000 |
| 9 | 40000 |
| 10 | 50000 |
| 11 | 55000 |
| 12 | 57000 |
| 13 | 59000 |
| 14 | 60000 |
| 15 | 60500 |
| 16 | 61000 |
| 17 | 61500 |
| 18 | 62000 |
| 19 | 62500 |
| 20 | 63000 |

Figure 4A:
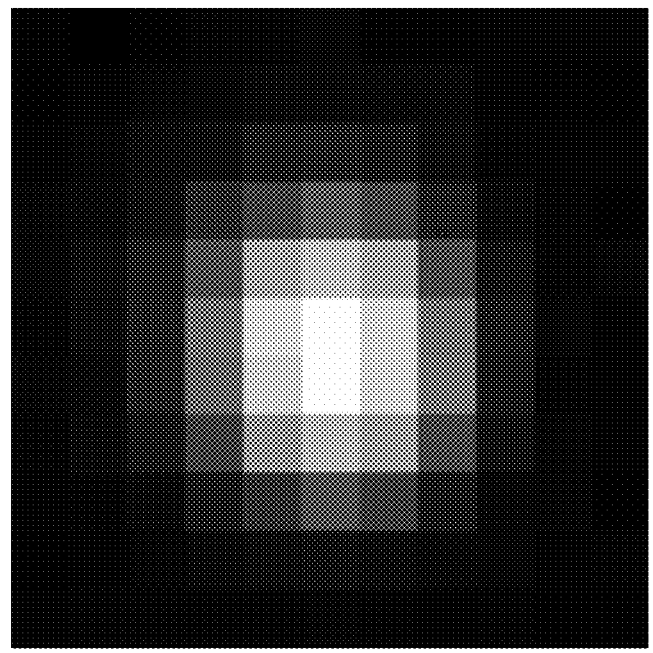
FIG. 4A is a measurement of a particle taken with a CCD detector.

In some embodiments, an individual particle may be measured and the measurement may be processed to increase the accuracy of the measurement. FIG. 4A is a figure showing the raw data from a measurement of a particle using a CCD detector. The figure is 11 pixels by 11 pixels and shows one particle. Although a center of the particle may be roughly discerned, the accuracy of the center may be at most a pixel or half pixel. The image is created by illuminating a particle with a light source 104. The particle 110 may have a fluorescent material either inside the particle or on the surface of the particle. The light 114 from the light source 104 may cause the fluorescent material to fluoresce and emit light 116. The light 116 may then be detected by the light detector 108. The light detector may be a CCD detector, which may then transmit information to the processor 118. The information shown in FIG. 4A is raw data, meaning that it is the information created by the light detector 108 before any processing. The processor 118 takes the raw data and manipulates the data to create useful output, such as information relating to the substance contained in the particles. In some embodiments, the processor may comprise more than one processor. For example, as shown in FIG. 1, the light detector 108 may have a processor that performs some amount of processing and communications of the information to the processor 118. The processor 118 may then take that information and further process it to create usable output.

Figure 4B:
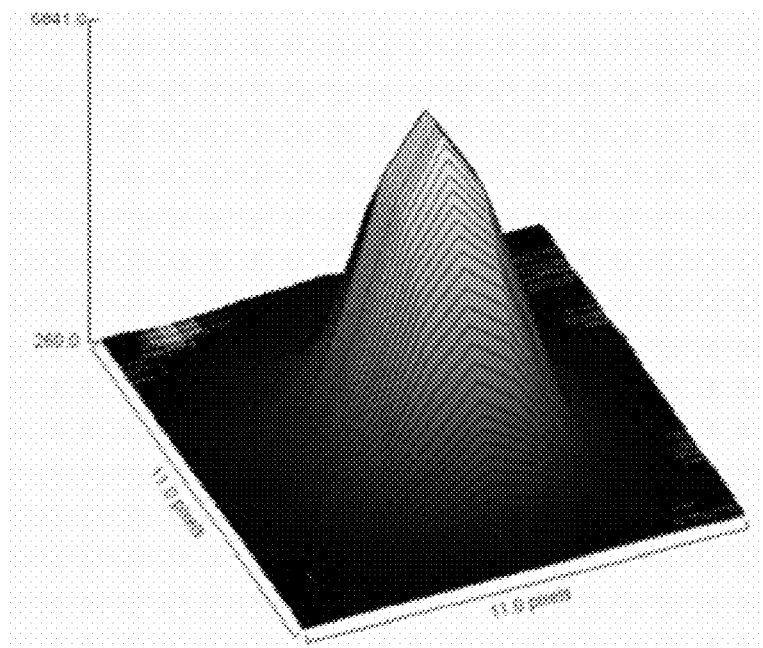
FIG. 4B is a three-dimensional graphical representation of the measurement shown in FIG. 4A.

FIG. 4B shows a three-dimensional graphical representation of the measured particle in FIG. 4A. As can be seen in FIG. 4B, the intensity of the particle is clearly higher at the center of the particle, but the actual position of the particle is not easily measured.

Figure 5A:
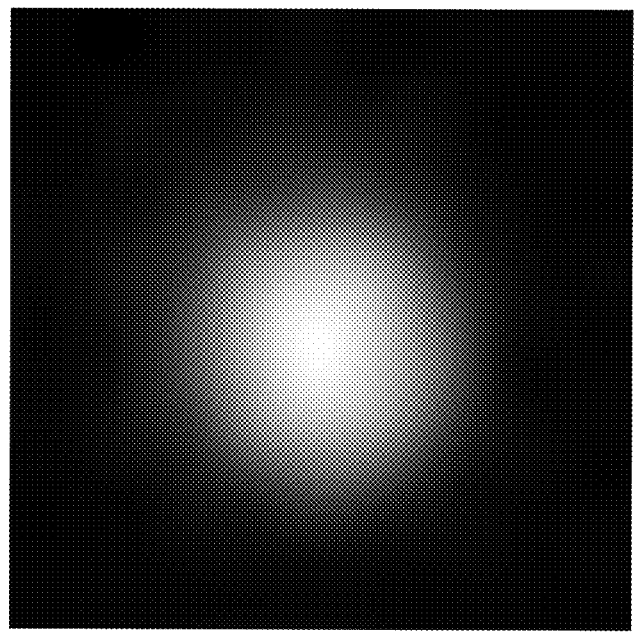
FIG. 5A is an interpolated image of the particle shown in FIG. 4A.

In one embodiment, the accuracy of the position of the particle is improved by interpolating the measurement of FIG. 4A to create the image of 5A. FIG. 5A shows an image having 110 pixels by 110 pixels. The information contained in FIG. 5A is calculated from the information in FIG. 4A using interpolation. In some embodiments, the interpolation used is spline interpolation. In some embodiments, the interpolation used is polynomial interpolation. Also, in some embodiments, only regions close to particle centers are interpolated, which may reduce the required resources of the system.

One advantage of using interpolation is that the center of the particle may be located with more precision. For example, in FIG. 5A the pixel having the highest intensity can be used to determine the center of the particle. Compared to FIG. 4A, the center of the particle may be determined with about 10-times more precision. One advantage of the system is that the centers of particles may be determined with more precision than may be possible with the detector alone. Therefore, a CCD detector with a limited resolution may give an output with increased resolution. This allows the system to have a CCD detector that is lower resolution, which may be cheaper or have lower noise, or it may allow the system to attain a resolution that is higher than the highest-resolution CCD detector available. Additionally, the interpolation method may help compensate for loss of resolution caused by optics. In some embodiments, lenses may help make a system more compact, but may adversely affect the resolution of the measured particles. Interpolation may offset the loss of resolution.

Figure 5B:
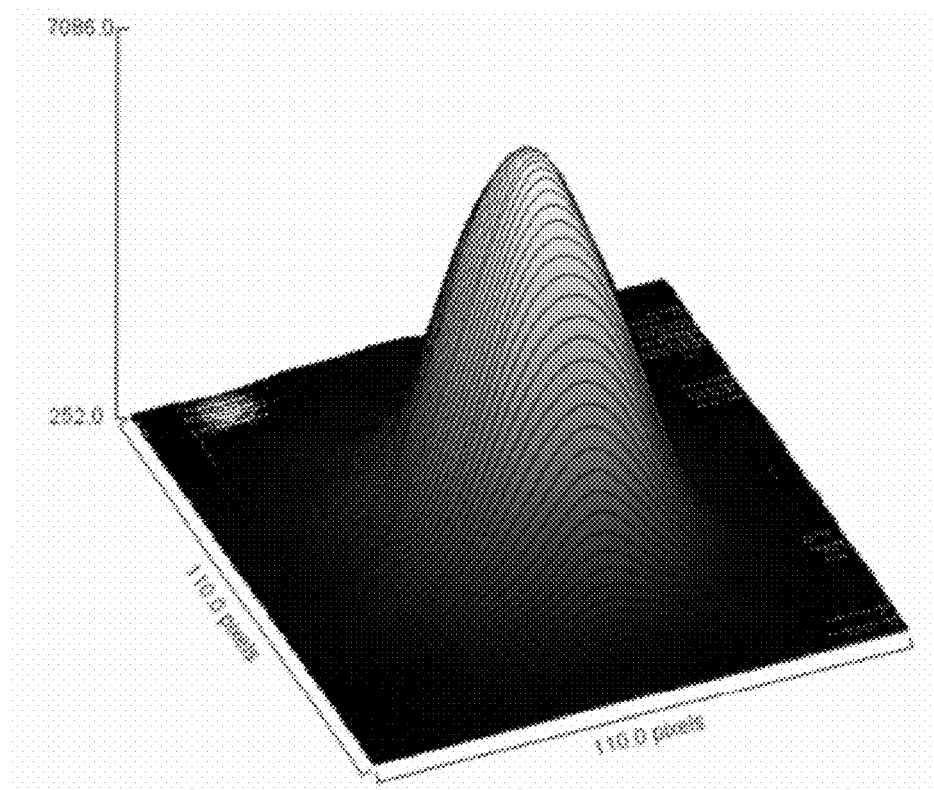
FIG. 5B is a three-dimensional graphical representation of the particle shown in FIG. 5A.

In some embodiments, the intensity of the particle may be calculated from the peak value of the particle because the expected distribution may be known. In some embodiments, the intensity of the particle may be measured by integrating the interpolated image, which may result in higher resolution of measured intensity. The measured intensity of the particle includes the sum of all of the pixels that receive light from the particle. Therefore, one method of finding the intensity is to add all of the pixel intensities together. Similar to a higher resolution in detecting the center of the particle, the intensity of the particle may be determined at a higher resolution by integrating the interpolated image. In particular, the intensity of the particle shown in FIG. 4B can be determined by adding the height of all of the pixels in FIG. 4B. Similarly, the height of all of the pixels in FIG. 5B can be added (and divided by 100 because there are 100 times more points in FIG. 5B than 4B) to find the intensity of the particle with increased resolution. Because the intensity of the measured particle can be determined with increased accuracy, the accuracy of the entire system is improved. Different intensity levels between different particles may be discerned which may allow different levels of absorption to be discerned between different particles. Because a goal of the system is to measure the amount of fluorescent material, the accuracy of the measurement of the intensity of the fluorescence is directly tied to the performance of the system.

In some embodiments, an analytical representation of a particle may be calculated using either the raw data image or the interpolated image. In this embodiment, a curve, such as a Gaussian curve may be fit to the measured points. The distribution of the curve may be Gaussian because of the point spread function of the lens. The expected curve, which may be represented as an equation or a matrix, may then be used to determine the center of the particle or the intensity of the particle. For example, the center of the particle is where the derivative of the curve equals zero. If there is more than one point where the derivative is equal to zero, the image may contain more than one particle. Also, the equation may be integrated around a certain radius of the center to determine the intensity of the particle.

The intensity at a point p having distance r from the center of a particle can be estimated by Eq. 1:

$$f(r) = a \times e^{b \times r^2} \qquad \text{Eq. 1}$$

where a and b are constants. Specifically, a is the peak intensity value at the center, and b is the rate of decay. The value b may be estimated at calibration time from a set of N data points $p_1 \ldots p_N$ using a least squares approach as shown in Eq. 2, $$\sum_{i=1}^{N} (\ln(f(\|p_i - c\|)) - \ln(\|p_i - c\|))^2 \qquad \text{Eq. 2}$$

where c is the particle center. Note that due to the nature of the logarithm, smaller values contribute more to the error than larger values. This has an effect of weighting the values closer to particle center higher than those values farther away. This weighting is appropriate because there are more points farther away from the center—as the radius $r_1$ increases to $r_2$ the number of pixels that fall within the circle increases by the square of the ratio $r_1/r_2$. Therefore, points closer to the center of the particle may be of more interest than points farther away.

Let I(p) be the intensity of a point p in the image. Let E(p) denote the error from the expected intensity f(p) as:

$$E(p) = N(\|p - c\|) \times \left( \frac{|I(p) - f(\|p - c\|)|}{\min\{I(p), f(\|p - c\|)\}} \right) \qquad \text{Eq. 3}$$

where N(r) is a normalizing function that acts to weigh pixels closer to the center higher than pixels farther away. One particular choice of N(r) is:

$$N(r) = \begin{cases} \frac{1}{\ln(r)} & r \geq e \\ 1 & 0 < r < e \end{cases} \qquad \text{Eq. 4}$$

In order to accept a particle for classification, one may require:

$$\forall\ p \in \{p_i\ \ldots\ p_N\}, E(p) < \varepsilon_1 \qquad \text{Eq. 5}$$

$$\sum_{i=1}^{N} (E(p_i)) < \varepsilon_2 \qquad \text{Eq. 6}$$

for some constant values $\varepsilon_1$ and $\varepsilon_2$ where points $p_1 \ldots p_N$ lie within a specified radius about the particle center.

In some embodiments a particle discriminator may be performed about a preferably sub-pixel accurate peak location in order to quantify whether the particle displays an assumed Gaussian shape intensity likeness. Given a set of pixels P within some specified radius of the particle's peak location q, an ideal imaged particle is assumed to display an intensity profile that models a Gaussian shape having the form of Equation 1, where r is the Euclidian distance from p element of P to q, a is the intensity value at q, and b is an intensity decay parameter having a negative sign. An algorithm for discriminating particles measures the error of intensity(p) versus $f(\|p-q\|)$ under some metric, and the accumulation of this error over every pixel in P to ensure the error is small enough to proceed. Otherwise, the particle can be discarded from further processing. Discrimination is preferably done in sub-pixel image coordinate space for greater accuracy.

Figure 6A:
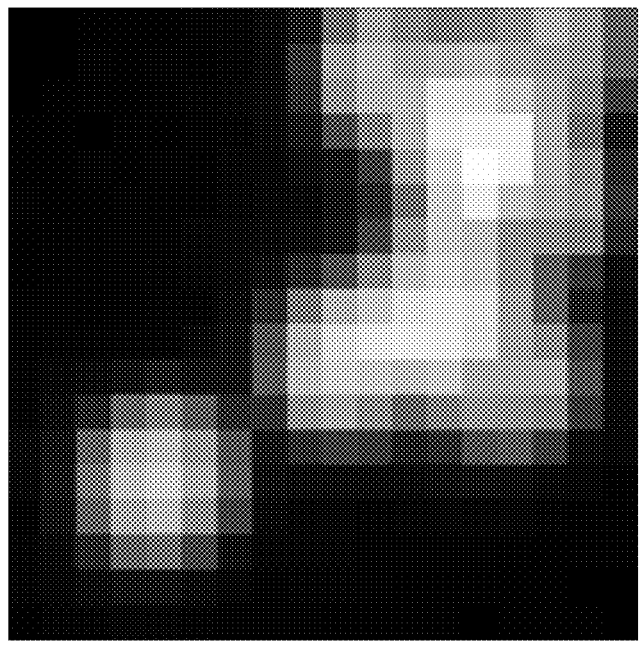
FIG. 6A is a measurement of several particles, where some particles are close together.
Figure 6B:
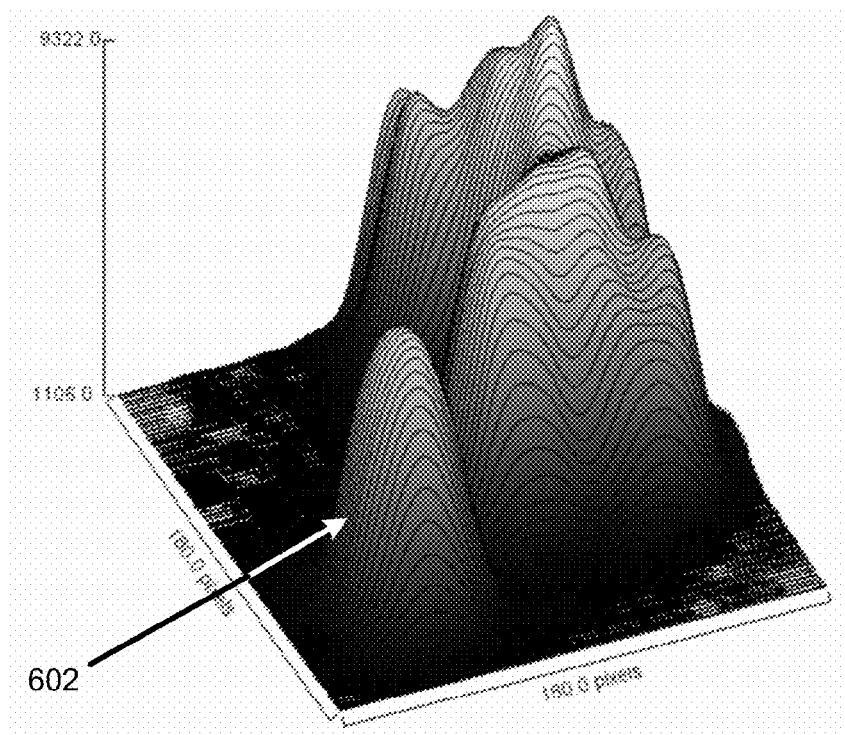
FIG. 6B is a three-dimensional graphical representation of an interpolated image based on the measured particles in FIG. 6A.

FIG. 6A shows the raw data of an image containing several particles. FIG. 6B shows the interpolated information in a three-dimensional rendering. Particle 602 may be accurately measured and may give reliable information about the intensity of the particle. However, the other particles may be too close together to provide reliable information. In one embodiment, the disclosed methods determine when particles should be considered and used in producing an output, and when they should be discarded. In one embodiment, an expected distribution is calculated based on the peak intensity of a particle and the known size of the particle. For example, if all of the particles are of a particular size, the Gaussian distribution of the measured light can be predicted. Therefore, by measuring the peak intensity of the particle, the rest of the shape of the particle can be estimated. The estimated shape can then be used to determine whether a measurement includes light from more than one particle. For example, an expected distribution may predict that a pixel that is two pixels away from the center of a particle should have 50% of the intensity of a the pixel at the center. Therefore, if a pixel that is two pixels away in any direction has 80% of the intensity of the center pixel, one may infer that there is another particle nearby. In this situation, one may determine that it is preferable to discard the measurement rather than integrate the particle to determine the intensity. If there is a nearby particle that is contributing light, the measured intensity will be artificially inflated and may lead to an inaccurate measurement.

Figure 7:
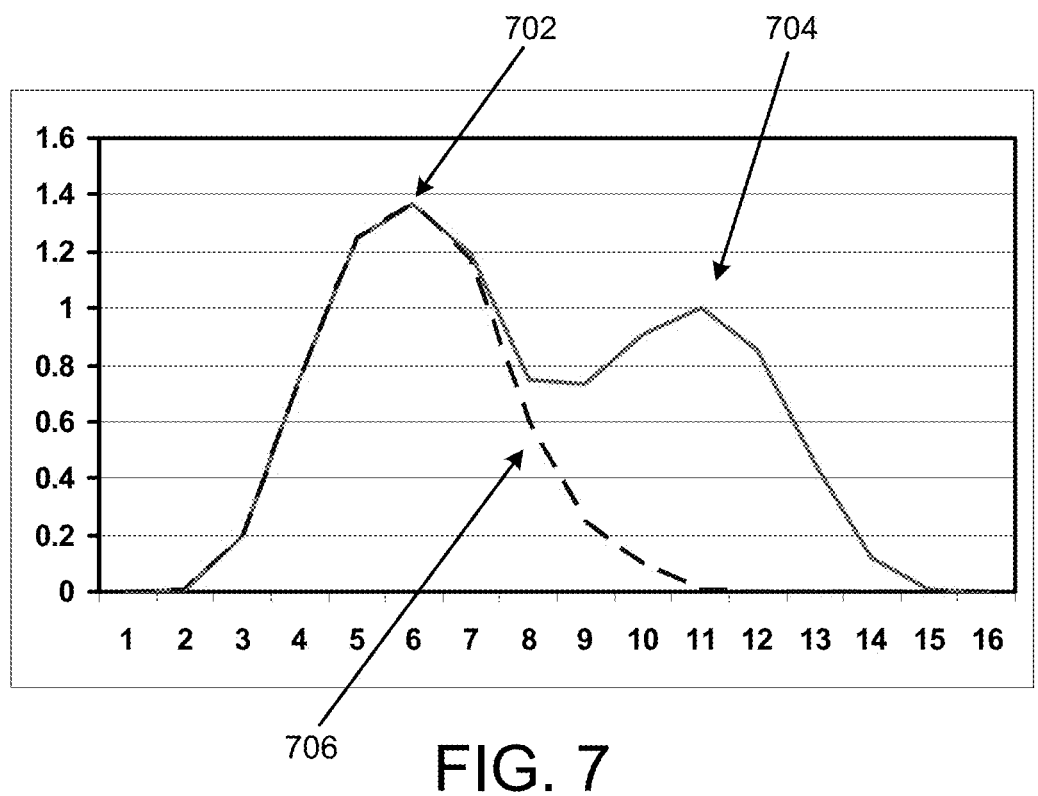
FIG. 7 is a graph showing the light distribution of two nearby particles.

FIG. 7 shows a graph of two particles 702 and 704 that are near each other measured by a light detector 108. The solid line shows the measured intensity of particles 702 and 704. The dashed line 706 shows the expected distribution of particle 702, which may be calculated by the peak of particle 702 and/or the slope on the left side of the particle 702. The dashed line 706 can be used to subtract the contribution of particle 702 to the measurement of particle 704. Alternatively, the dashed line 706 can be used to determine when the measurement of particle 702 and/or 704 should be discarded.

In some embodiments, more than one image is taken of a set of particles. For example, a second light source 106 may be used to take a third image, where the second light source 106 emits light 115 at a different wavelength than the light 114 from the first light source 104. Because the second light source 106 emits light 115 at a different wavelength, it may be used to detect a second type of fluorescent material that may be present in particles 110. Therefore, if a particle 110 has a material that fluoresces under the light of the second light source 106, but not under the light of the first light source 104, the third image may have a particle in a location where the first image does not. However, in some cases, the a single particle may be measured in both the first image and the third image, and can be used to align the first image and the third image. For example, if the first image and the third image are offset by a few pixels, they can be aligned if the center of a particle in the first image is offset from the center of the same particle in the third image. In some embodiments, more than one particle may be used to align different images. In some embodiments, many particles may be used to align the images, where the offsets measured from many particles are averaged. In some embodiments, some offsets may be discarded because they may represent erroneous measurements and the rest of the offsets may be averaged.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 8:
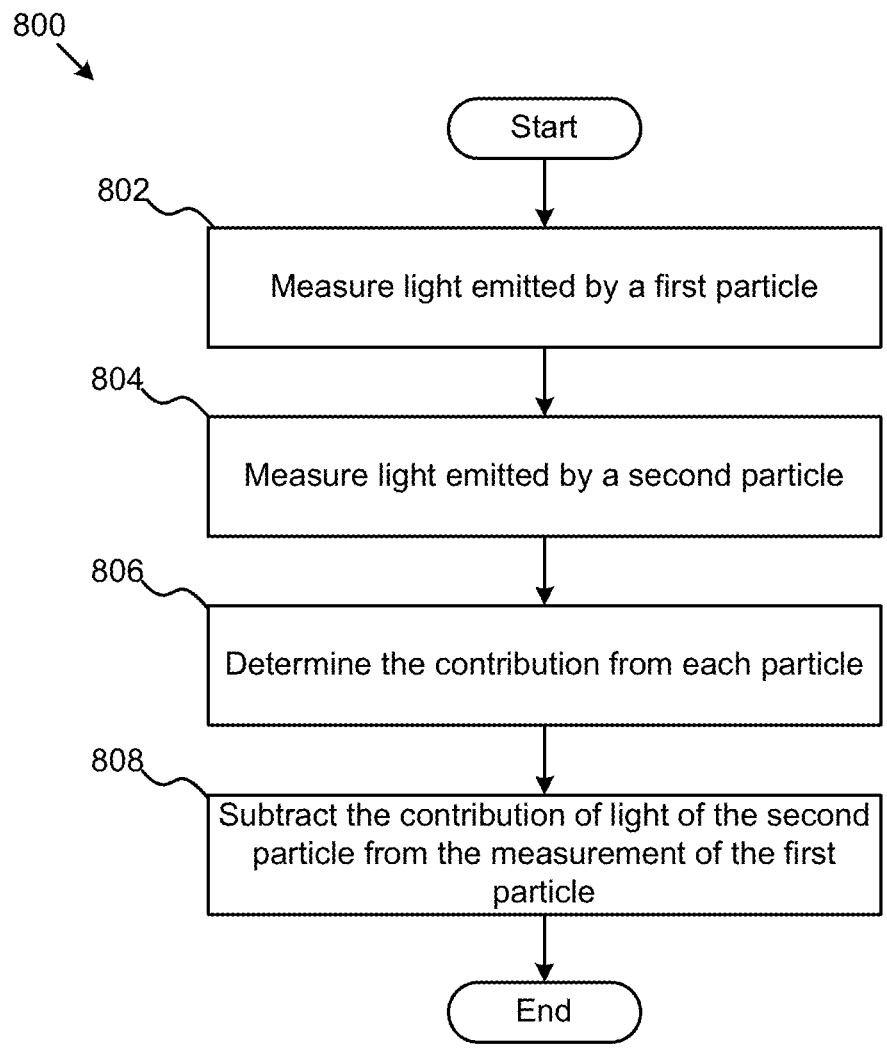
FIG. 8 is a flow chart diagram representing a method for subtracting the contribution of light of one particle from another.

FIG. 8 illustrates one embodiment of a method 800 for increasing the accuracy of measurement in imaging cytometry. In one embodiment, the method 800 starts at step 802. In step 802, a light source 104 is used to illuminate a particle 110 which then fluoresces and emits light that is measured in detector 108. In step 804, the light from a second particle is measured using the same light detector 108. In some embodiments, the measurements of 802 and 804 are accomplished simultaneously. In step 806, the contribution of light from each particle is determined. In some embodiments, this step of determining the contribution of light from a particle includes calculating the expected distribution of the light based on the known parameters and measured parameters. For example, a known parameter may be the radius of the particle. A measured parameter may be the peak intensity of the particle. Using a known parameter and a measured parameter, one may calculate the expected distribution of the particle. For example, the expected distribution may be Gaussian, as represented in Eq. 1. In some embodiments, the expected distribution may be determined by calculating an analytical representation of a particle. In some embodiments, a heuristic may be used that approximates the expected distribution. For example, one may approximate that the intensity of a pixel should decrease by a particular percentage depending on how far from the center of the particle a pixel is.

In step 808, using the expected distribution, one may subtract the contribution of one particle from the measurement of another particle.

In some embodiments, an inter-image alignment step may be performed in order to ensure each particle is associated with the correct location in every image channel where the alignment error is assumed to be a translation T of the image coordinates in the x and/or y directions. When a peak search can be performed in an image channel, the inter-image alignment algorithm aligns the detected peaks across the image channels. When a peak search can be performed in some but not all image channels, the inter-image alignment algorithm instead uses the mean location q of a peak value across all channels where the peak was found as an initial value for the location of the particle in the channel c where a peak search cannot be performed. Then this position q is refined in c by allowing q to be perturbed in 1/s sub-pixel steps by up to +/−r pixels along both axes and taking the perturbed value p that yields a maximal optical parameter. For every particle the inter-image particle shift is calculated as the vector q-p and this vector is recorded. Thus each particle votes for its preferred alignment shift. After all the particles have voted for their respective preferred alignment shifts, a statistically significant global shift satisfying the translation T can be seen as the predominant cluster in this vector vote space. The predominant cluster is located, and the center of mass of this cluster is computed as the inter-image alignment vector satisfying T.

In some embodiments, the inter-image alignment step may include finding the centers of multiple particles by using bounding squares or circles. According to one method, all possible bounding squares of a particular size (e.g. 5 pixels×5 pixels) are summed and the squares with sums higher than a predetermined value are considered to encompass the center of a particle. This technique may be more accurate than simply finding a maximum pixel magnitude in cases where the distribution of surface dye is not uniform across the area of the particle. For example, if the fluorescent dye molecules are unevenly distributed on the surface of the particle, the maximum light emitted from the dye may not come from the center of the particle and the measured light may not have a Gaussian distribution.

FIGS. 11A-11E show some embodiments of a bounding area method. The first embodiment described is a method using a bounding square of varying length. If the optical parameter chosen involves taking the sum of the pixel values according to a constraint Z, where Z specifies those pixel values inside a bounding square of length $2*w+1$ centered at p where some fixed value r is an upper bound for all w, the sum should be computed efficiently by pre-computing a sums matrix as follows.

Let $L=s*k+r$. All pixels that fall within a bounding square of length $N=2*L+1$ centered at p are copied to a temporary matrix M which is buffered with 0's on both the left (minimum x) and upper (minimum y) boundaries (Step A).

Consider row R of length N+1 of matrix M where we denote $R[-1]$ to be the 0 entry at the left. For each R in M do the following:

Initialize the sum to 0.

For each integer i from 0 to N−1

Update sum=sum+$R[i]$

Assign $R[i]$=sum                                   (Step B0)

For any given k, $R[k]$ denotes the sum of all the values to the left and including k in row R of matrix M.

Now consider column C of length N+1 of matrix M where we denote $C[-1]$ to be the 0 entry at the top. For each C in M do the following:

Initialize the sum to 0.

For each integer i from 0 to N−1

Update sum=sum+$C[i]$

Assign $C[i]$=sum                                   (Step C0)

Now the sum of all the pixels in the image about a bounding box of length $2*w+1$ centered at p=<x,y> can be computed as:

$$\text{sum}=M[u1,v1]+M[u0,v0]-M[u1,v0]-M[u0,v1] \quad \text{(Step D0)}$$

where: $u0=(p-q)\cdot x+L-w-1$, $v0=(p-q)\cdot y+L-w-1$
$u1=(p-q)\cdot x+L+w$, $v1=(p-q)\cdot y+L+w$ The position p that obtains the maximum sum can now be determined efficiently.

Figure 11A:
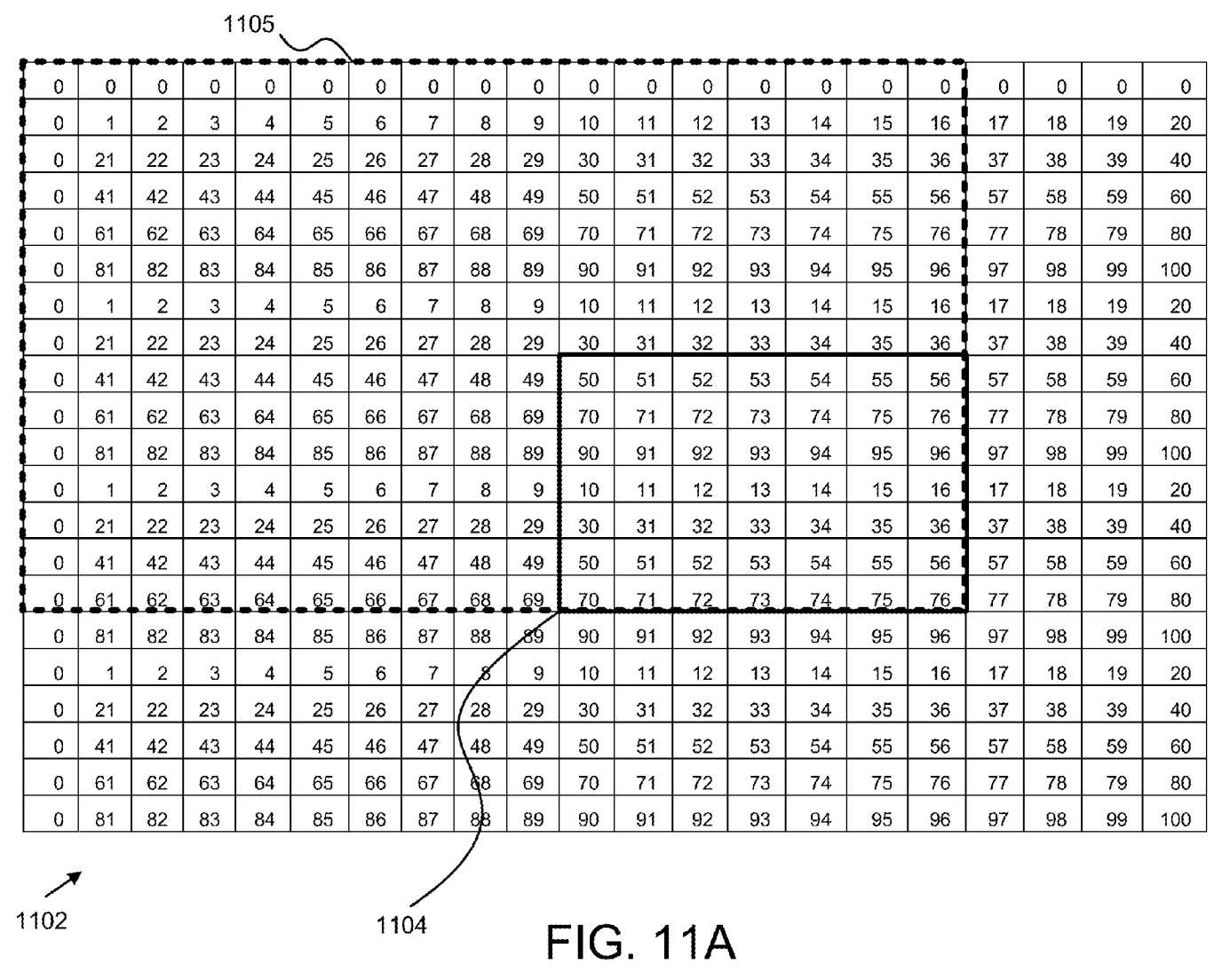

As an example, consider a matrix 1102 as shown in FIG. 11A after copying the pixel values in Step A, where the goal is to find the sum of pixels inside the bounded square 1104. After performing the sums for each row and column as described in steps B0 and C0, one gets the matrix 1106 as shown in FIG. 11B, where each cell corresponds to a pixel in FIG. 11A and contains the sum of itself and all pixels above and to the left of itself. For example, square 1108 in FIG. 11B is the sum of all pixels in square 1105 in FIG. 11A. Once the matrix 1106 has been computed, it becomes faster to compute sums of bounded squares. For example, to find the sum of bounded square 1104 in FIG. 11A (which corresponds to bounded square 1118 in FIG. 11C), one can simply take square 1108 minus square 1112, minus square 1116, plus square 1114. In this example, 10224−5310−4472+2295=2737, which is the sum of all the pixels in bounded square 1104 in FIG. 11A. One advantage of using the bounded squares method is that it is faster to find the sum of all possible bounded squares while still providing the advantage of using bounded squares over simply using maxima.

In another embodiment, bounding squares of a fixed length are used. The sums of the bounded squares may be computed and stored in a matrix. For example, if the constraint Z imposed upon the pixels as input to the optical parameter specifies the pixels inside a bounding square of length $2*r+1$ centered at p where r is a fixed integer>=1 then Step B can be modified as follows:

Consider row R of length N+1 of matrix M where we denote $R[-1]$ to be the 0 entry at the left. Let R' be the new row R of M. For each R in M do the following:

Let $w=2*r$

Initialize the sum to 0.

For each integer i from 0 to w−1

Update sum=sum+$R[i]$

Assign $R'[i]$=sum

For each value i from w to N−1

Update sum=sum+$R[i]$

Assign $R'[i]$=sum

Update sum=sum−$R[i-w]$                      (Step B1)

Step C can be modified as follows:

Consider column C of length N+1 of matrix M where we denote $C[-1]$ to be the 0 entry at the top. Let C' be the new column C of M. For each C in M do the following:

Let $w=2*r$

Initialize the sum to 0.

For each integer $i$ from 0 to $w-1$

Update sum=sum+$C[i]$

Assign $C'[i]$=sum

For each integer $i$ from $w$ to $N-1$

Update sum=sum+$C[i]$

Assign $C'[i]$=sum

Update sum=sum−$C[i-w]$ (Step C1)

Now the sum of all the pixels in the image about a bounding box of length $2*r+1$ centered at p=<x,y> can be determined as:

sum=$M[u1,v1]$ (Step D1)

where $u1=(p-q)\cdot x+L+r$, and $v1=(p-q)\cdot y+L+r$

Figure 11D:
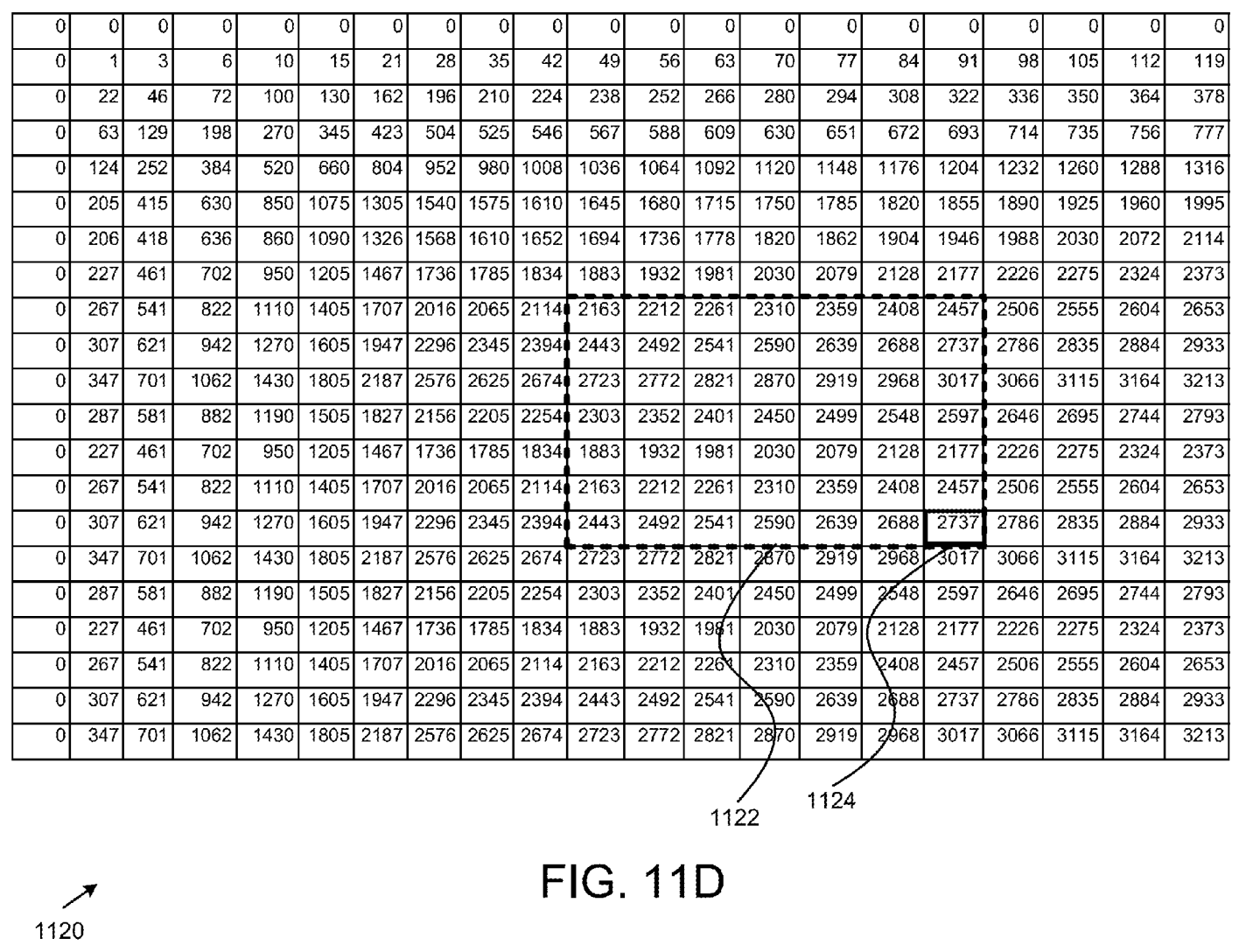

For example, after steps B1 and C1 have been computed on matrix 1102, one gets matrix 1120 in FIG. 11D. To find the sum of the pixels corresponding to bounded square 1122, one can simply look at square 1124. One advantage of using this method is that finding the sum of bounded squares takes very little resources or time after the matrix 1120 has been computed.

In a third embodiment, a bounded circle of varying diameter may be used. In this embodiment, if the constraint Z imposed upon the pixels as input to the optical parameter specifies pixels within a closed circle centered at p with diameter $2*r+1$ (where r is an iteger>=1), then one may perform steps A and B0 to C0 as described obtain a matrix 1106 in FIG. 11B. Next, the sum of all the pixels in the image about within a closed circle of diameter $2*r+1$ centered at p=x,y can be determined by performing the following step:

Let $u=(p-q)\cdot x+L$

Let $v=(p-q)\cdot y+L$

Initialize sum=0

/*Compute the contribution of the horizontal line of pixels through the center*/

Update sum=sum+$M[u+r,v]-M[u-r-1,v]$

For each $y$ from 1 to $r$

//Determine the intersection of the horizontal line with the circle

Let $s$=floor($sqrt(r^2-y^2)$)

//Compute the contribution of the horizontal line below the center

Update sum=sum+$M[u+s,v+y]-M[u-s-1,v+y]$

//Compute the contribution of the horizontal line above the center

Update sum=sum+$M[u+s,v-y]-M[u-s-1,v-y]$. (Step D2)

In another embodiment, a bounding circle of a fixed diameter may be used. In some embodiments, a circle may give a better fit to the profiles of particles. Using this embodiment, if the value r for the diameter $2*r+1$ for the above constraint Z is fixed, then the intersection points of each horizontal line with the circle can be pre-computed and stored in a table. Thus, step D can be rewritten as:

Let $u=(p-q)\cdot x+L$

Let $v=(p-q)\cdot y+L$

Initialize sum=0

/*Compute the contribution of the horizontal line of pixels through the center*/

Let $s$=Table[0]

Update sum=sum+$M[u+s,v]-M[u-s-1,v]$

For each $y$ from 1 to Table·Length−1

//Get the intersection points of the line with the circle by lookup

Let $s$=Table[$y$]

//Compute the contribution of the horizontal line below the center

Update sum=sum+$M[u+s,v+y]-M[u-s-1,v+y]$

//Compute the contribution of the horizontal line above the center

Update sum=sum+$M[u+s,v-y]-M[u-s-1,v-y]$ (Step D3)

Where the table is generated once during initialization by the following step:

Set Table·Length=$r+1$

For each $y$ from 0 to $r$

Table[$i$]=floor($sqrt(r^2-y^2)$)

Figure 9:
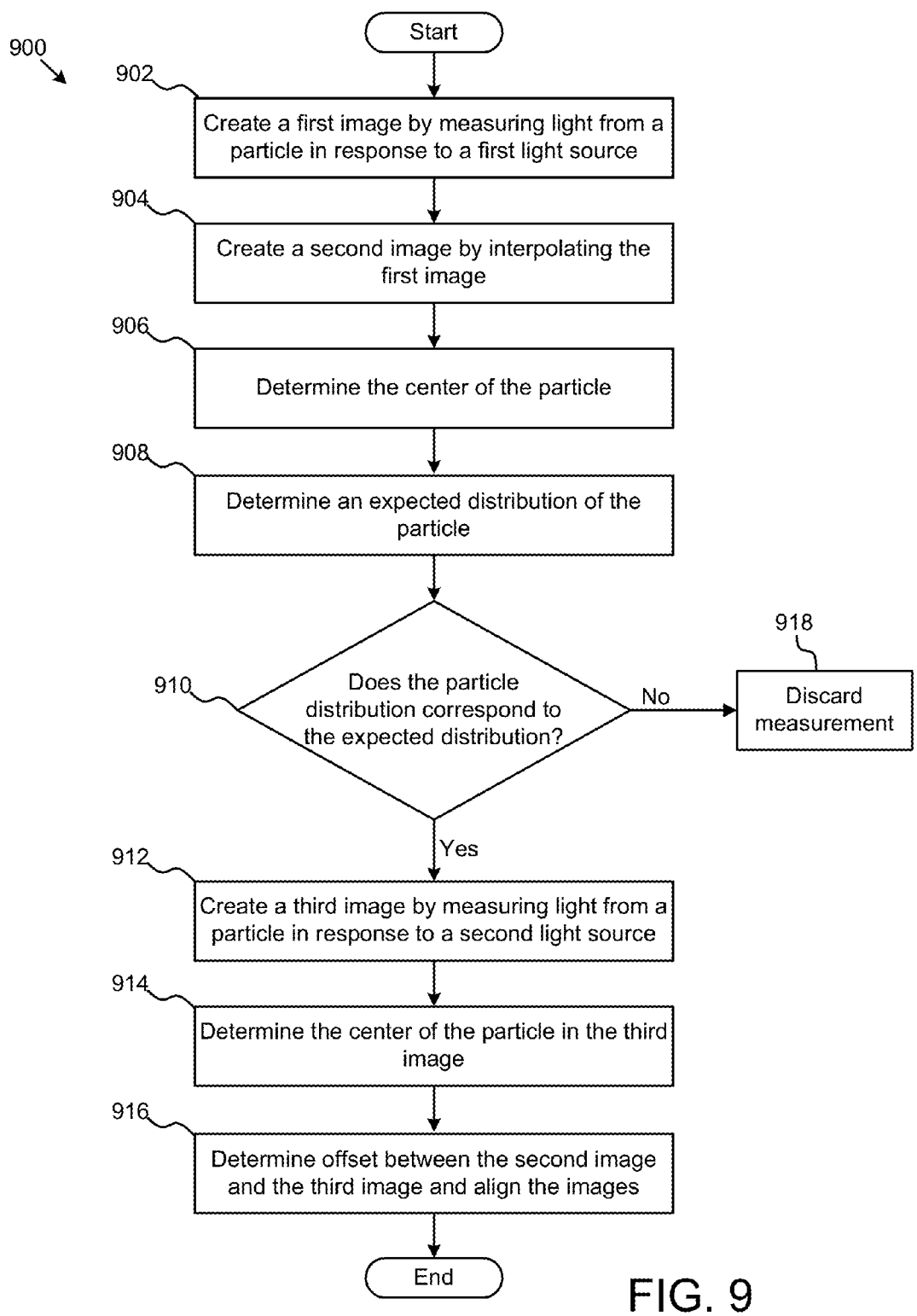
FIG. 9 is a flow chart diagram representing a method for improving the accuracy of a image cytometry measurement.

FIG. 9 shows a schematic block diagram for a method 900 for determining whether to use a measured particle, and how to align two images. In step 902, a first image is created by measuring the light emitted from a particle 110 in response to illumination from a light source 104. In step 904, the first image is interpolated to create a second image. In some embodiments, the interpolation used is spline interpolation. In step 906, the center of the particle is determined. The center of the particle may be determined by finding the pixel in the second image with the highest value. The center of the particle may also be determined by creating an analytical representation of the particle. The derivative may be set to zero and the equation solved for the location of the center. In step 908, the expected distribution of the particle may be determined. In some embodiments, the expected distribution may be a Gaussian distribution. At step 910, the measurement of the particle can be compared to the expected distribution. If the measurement of the particle does not correspond to the expected distribution, the measurement may be discarded at step 918.

In step 912, a third image may be created. The third image may be created by shining a second light 106 source onto the particles, where the second light source 106 emits light 115 at a different wavelength than the first light source 104. In step 914, the center of the particle may be determined in the third image. In some embodiments, this step may further include interpolating the third image to create an image having increased resolution. This method may be similar to the method used to create the second image from the first image. In step 916, an offset between the second image and the third image is calculated. In some embodiments, this step includes finding at least one particle that is present in both images and determining the offset. Finally, the second and third images are aligned based on the offset calculated between the images.

Figure 10:
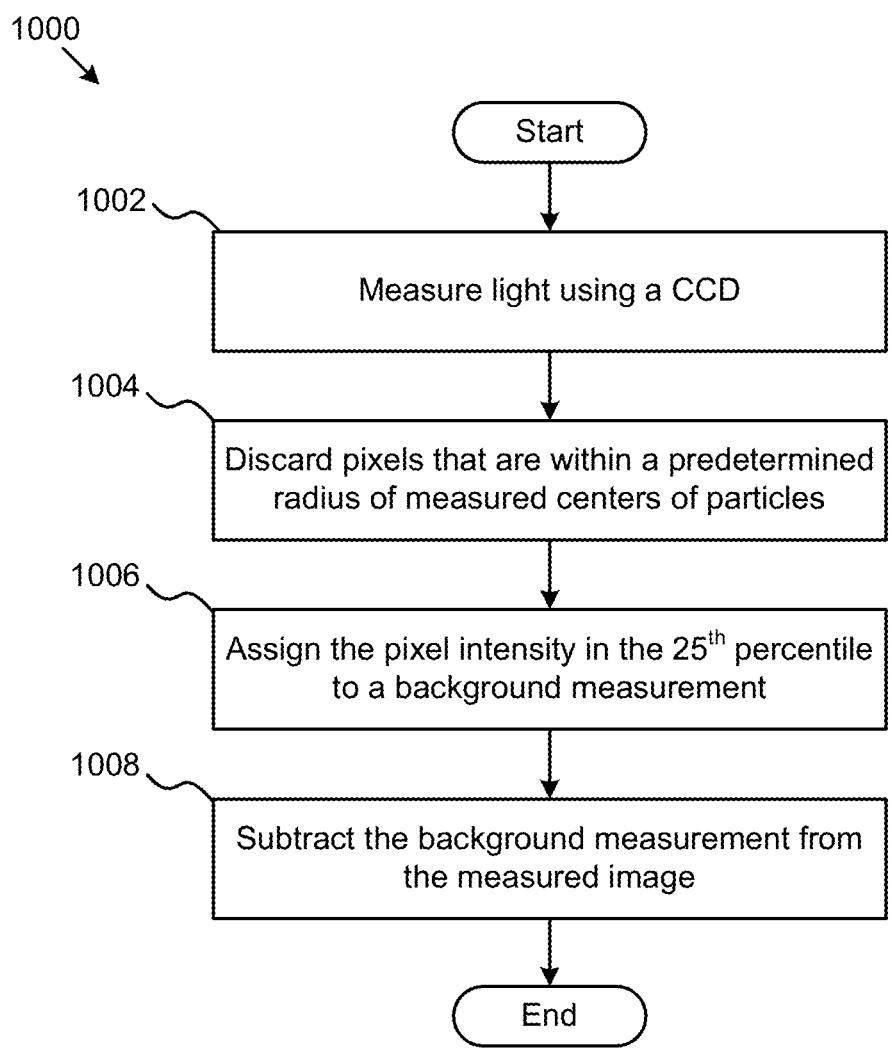
FIG. 10 is a flow chart diagram representing a method for determining the intensity of a background signal in a cytometry image.

In FIG. 10, a method 1000 is described for increasing the accuracy of an imaging cytometry by accurately measuring a background signal. In step 1002, light from a particle 110 is measured using a light detector 108, such as a CCD detector, in response to light from a light source 104. A measurement using a CCD detector may include both a measurement of particles and a measurement of background signal. The background signal may include background light and may also include noise.

In optional step 1004, pixels that are within a predetermined radius of measured particles are discarded. The center of the particles may be determined as described above, and the radius may be fixed. In some embodiments, the radius of excluded pixels may increase with the intensity of light from the particle. Therefore, in some embodiments, the brighter a particle, the more pixels that are discarded. Because a goal is to measure the background signal, the measurement of the particles may not be useful.

In step 1006 the background measurement is assigned as the measured intensity of the pixel that is in the $25^{th}$ percentile. In one embodiment, all pixels (including the measured particles) in an image are sorted and placed in order. In some embodiments, as described in step 1004, pixels that are within a predetermined radius of a center of a particle are discarded and the remaining pixel intensities are placed in order. By placing the pixels in order, the darker pixels are placed at one end of a list and the lighter pixels are placed at the other. Because the measurement in each pixel will have a noise component, the darkest pixels on the list are the background signal plus a negative noise signal. Pixels higher up in the list will be just the background signal with little to no noise. Even higher in the list are pixels with background signal plus a positive noise component. Finally, the pixels at the top of the list may be pixels that have received light from a light source, such as a particle (although these pixels may be minimized by step 1004). Then, the intensity of the pixel that resides at the $25^{th}$ percentile is assigned as the background signal. For example, if the image consisted of 100 pixels, and all 100 pixels were sorted and entered into a list. The $25^{th}$ pixel from the bottom (the $25^{th}$ darkest pixel) would be assigned as the background level. One advantage of using the $25^{th}$ percentile is that it is closer to the low end, which will tend to not include light from light sources such as particles. However, by not being at the very bottom, the measurement includes little to no noise. Additionally, because the step 1006 only requires that the pixels be sorted and one pixel selected, the step requires relatively little processing power and resources. In some embodiments, a different percentile may be used. For example, in a low noise system, the $10^{th}$ percentile may provide an accurate background signal. In other systems, the $30^{th}$ percentile may be used. In some embodiments, the numbers are not actually placed in a list. Instead, the method may find value in the desired percentile by using an ordered statistics method. In some embodiments, the method of calculating the background noise may be computed for a region that is smaller than the entire detector. For example, the detector area may be partitioned into six different sectors and a background signal may be computed, according to the method described, independently for each sector.

In step 1008, the background signal determined in step 1006 can be subtracted from all pixels. By subtracting the background signal, the only signal left is the measured signal of the particles.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

What is claimed is:

1. A method, comprising:
   illuminating a particle using a first light source;
   creating a first image based on a first measurement of light emitted from the particle in response to illumination of the particle by the first light source, wherein the first measurement is performed by a light detector;
   creating a second image by interpolating between pixels in the first image, wherein the second image has a higher resolution than the first image;
   identifying a portion of the second image corresponding to a location of the particle;
   comparing the portion of the second image corresponding to the location of the particle to an expected distribution for the light emitted from the particle in response to the illumination;
   determining a difference between pixels of the second image and the expected distribution; and
   discarding the first measurement of light if the difference is above a selected threshold.

2. The method of claim 1, further comprising determining an intensity corresponding to the particle by integrating the second image.

3. The method of claim 1, further comprising creating an analytical representation of the first measurement of light and determining an intensity corresponding to the particle by integrating the analytical representation.

4. The method of claim 1, wherein the expected distribution is a Gaussian distribution.

5. The method of claim 1, further comprising:
   illuminating the particle with a second light source;
   creating a third image based on a second measurement of light emitted by the particle in response to illumination of the particle by the second light source, wherein the second measurement is performed by the light detector;
   identifying a portion of the third image corresponding to a location of the particle;
   determining a difference in location between the portion of the second image corresponding to the location of the particle and the portion of the third image corresponding to the location of the particle; and
   calculating an offset between the second image and the third image in response to the difference.

6. The method of claim 5, further comprising aligning the first image and the third image based on the offset.

7. The method of claim 5, further comprising using a plurality of particles to calculate the offset between the second image and the third image.

8. A non-transitory, computer-readable medium comprising program code that, when executed by a computer, causes the computer to perform operations comprising:
   causing a particle to be illuminated using a first light source;
   creating a first image based on a first measurement of light emitted from the particle in response to illumination of the particle by the first light source, wherein the first measurement is performed by a light detector;
   creating a second image by interpolating pixels in the first image, wherein the second image has a higher resolution than the first image;
   identifying a portion of the second image corresponding to a location of the particle;
   comparing the portion of the second image corresponding to the location of the particle to an expected distribution for the light emitted from the particle in response to the illumination;
   determining a difference between pixels of the second image and the expected distribution; and
   discarding the first measurement of light if the difference is above a selected threshold.

9. The non-transitory, computer-readable medium of claim 8, wherein the operations further comprise determining an intensity corresponding to the particle, wherein the intensity is based at least in part on light reflected by the particle, wherein the light reflected by the particle is incident upon the particle from at least one other particle.

10. The non-transitory, computer-readable medium of claim 9, wherein the determined intensity is further based on a determination that a central portion of the particle in the first image has a lower intensity than a perimeter portion of the particle in the first image.

11. The non-transitory, computer-readable medium of claim 8, wherein the operations further comprise discarding pixels that are within a selected radius of the particle.

12. The non-transitory, computer-readable medium of claim 8, wherein the operations further comprise determining a background intensity based on statistics of the pixels in the second image.

13. The non-transitory, computer-readable medium of claim 12, wherein the background intensity is determined by ordering the pixels in the second image based on intensity and assigning the background intensity to a selected percentile level in the ordered pixels.

14. The non-transitory, computer-readable medium of claim 13, wherein the selected percentile level is the 25th percentile.

15. The non-transitory, computer-readable medium of claim 14, further comprising subtracting the determined background intensity from the pixels in the second image.

16. An optical analysis system, comprising:
   a first light source configured to illuminate a particle;
   at least one light detector configured to measure light emitted by the particle in response to the illumination of the particle by the first light source;
   a processor coupled to the at least one light detector, wherein the processor is configured to:
      create a first image based on a first measurement of light emitted by the particle in response to illumination of the particle by the first light source;
      create a second image by interpolating between pixels in the first image, wherein the second image has a higher resolution than the first image;
      identify a portion of the second image corresponding to a location of the particle;
      compare the portion of the second image corresponding to the location of the particle to an expected distribution for the light emitted from the particle in response to the illumination;
      determine a difference between pixels of the second image and the expected distribution; and
      discard the first measurement of light if the difference is above a selected threshold.

17. The optical analysis system of claim 16, wherein the processor is further configured to determine an intensity corresponding to the particle by integrating the second image.

18. The optical analysis system of claim 16, wherein the processor is further configured to create an analytical representation of the first measurement of light and determine an intensity corresponding to the particle by integrating the analytical representation.

19. The optical analysis system of claim 16, wherein the expected distribution is a Gaussian distribution.

20. The optical analysis system of claim 16, wherein the system further comprises a second light source configured to illuminate the particle, and wherein the processor is further configured to:
   create a third image based on a second measurement at the at least one light detector of light emitted by the particle in response to the illumination of the particle by the second light source;
   identify a portion of the third image corresponding to a location of the particle;
   determine a difference in location between the portion of the second image corresponding to the location of the particle and the portion of the third image corresponding to the location of the particle; and
   calculate an offset between the second image and the third image in response to the difference.

21. The optical analysis system of claim 20, wherein the processor is further configured to align the first image and the third image.

22. The optical analysis system of claim 16, wherein the processor is further configured to use a plurality of particles to calculate the offset between the second image and the third image.

* * * * *